(12) United States Patent
Cunningham

(10) Patent No.: US 7,998,170 B2
(45) Date of Patent: Aug. 16, 2011

(54) SHARPOINT NEEDLE

(75) Inventor: Scott Cunningham, Cheshire, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1425 days.

(21) Appl. No.: 10/677,208

(22) Filed: Oct. 2, 2003

(65) Prior Publication Data
US 2004/0106948 A1 Jun. 3, 2004

Related U.S. Application Data

(60) Provisional application No. 60/416,330, filed on Oct. 4, 2002.

(51) Int. Cl.
A61B 17/08 (2006.01)

(52) U.S. Cl. ...................................... 606/223

(58) Field of Classification Search .................. 606/222, 606/223, 224
See application file for complete search history.

(56) References Cited

U.S. PATENT DOCUMENTS

| 20,409 | A | * | 6/1858 | Cottrill | 223/102 |
|---|---|---|---|---|---|
| 3,636,955 | A | * | 1/1972 | Kurtz | 606/223 |
| 4,128,351 | A | * | 12/1978 | Kurtz et al. | 606/223 |
| 4,513,747 | A | * | 4/1985 | Smith | 606/223 |
| 4,527,564 | A | | 7/1985 | Eguchi et al. | |
| 4,905,695 | A | | 3/1990 | Bendel et al. | |
| 4,932,961 | A | | 6/1990 | Wong et al. | |
| 4,959,068 | A | | 9/1990 | Bendel et al. | |
| 4,976,727 | A | | 12/1990 | Matsutani et al. | |
| 5,002,565 | A | * | 3/1991 | McGregor | 606/223 |
| 5,030,228 | A | * | 7/1991 | Wong et al. | 606/223 |
| 5,041,127 | A | | 8/1991 | Troutman | |
| 5,100,431 | A | | 3/1992 | Buster et al. | |

(Continued)

FOREIGN PATENT DOCUMENTS
EP 0 437 329 A2 7/1991
(Continued)

OTHER PUBLICATIONS

European Search Report for EP 03808130.3-2310 date of completion is Oct. 28, 2010 (3 pages).

Primary Examiner — Gary Jackson
Assistant Examiner — Jonathan A Hollm

(57) ABSTRACT

A surgical needle includes an elongated needle body defining a longitudinal axis, and having a main shaft, a needle end adjacent the main shaft, and a needle tip extending from the needle end and having an extreme needle point. The needle end includes a plurality of concave surfaces extending from the needle tip to the main shaft. The needle tip includes a plurality of concave surfaces extending from the needle point to intersect the concave surfaces of the needle end. The concave surfaces of the needle end are obliquely arranged relative to the longitudinal axis at a first angle. The concave surfaces of the needle tip are obliquely arranged relative to the longitudinal axis at a second angle greater than the first angle. The elongated needle body includes cutting edges disposed along lines of intersection of the concave surfaces of the needle end with the concave surfaces of the needle tip. The needle end includes four intersecting concave surfaces and defines a generally diamond-shape in cross-section along an axis transverse to the longitudinal axis. The needle end defines a maximum cross-sectional dimension greater than a corresponding maximum cross-sectional dimension of the main shaft. The needle tip may include four intersecting concave surfaces and define a general diamond shape cross-section.

15 Claims, 5 Drawing Sheets

U.S. PATENT DOCUMENTS

| | | | |
|---|---|---|---|
| 5,178,628 A | 1/1993 | Otsuka et al. | |
| 5,263,974 A | 11/1993 | Matsutani et al. | |
| 5,330,441 A | 7/1994 | Prasad et al. | |
| 5,403,344 A * | 4/1995 | Allen | 606/223 |
| 5,464,422 A | 11/1995 | Silverman | |
| 5,476,480 A | 12/1995 | Matsutani et al. | |
| 5,683,415 A | 11/1997 | Brunken | |
| 5,683,416 A * | 11/1997 | McGregor et al. | 606/223 |
| 5,725,555 A | 3/1998 | Moll | |
| 5,749,897 A | 5/1998 | Matsutani et al. | |
| 5,797,961 A * | 8/1998 | Smith et al. | 606/222 |
| 5,853,423 A | 12/1998 | McGregor et al. | |
| 5,891,164 A | 4/1999 | Dabir et al. | |
| 5,897,764 A | 4/1999 | Schulsinger et al. | |
| 5,928,268 A | 7/1999 | Butwell et al. | |
| 6,019,781 A | 2/2000 | Worland | |
| 6,129,741 A | 10/2000 | Wurster et al. | |
| 6,252,195 B1 | 6/2001 | Mosavi et al. | |
| 6,322,581 B1 * | 11/2001 | Fukuda et al. | 606/223 |

FOREIGN PATENT DOCUMENTS

EP    0 443 704 A1    8/1991

* cited by examiner

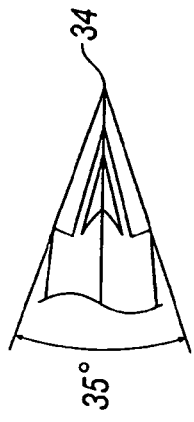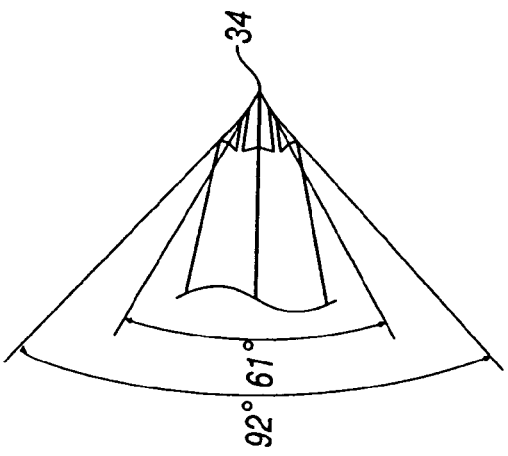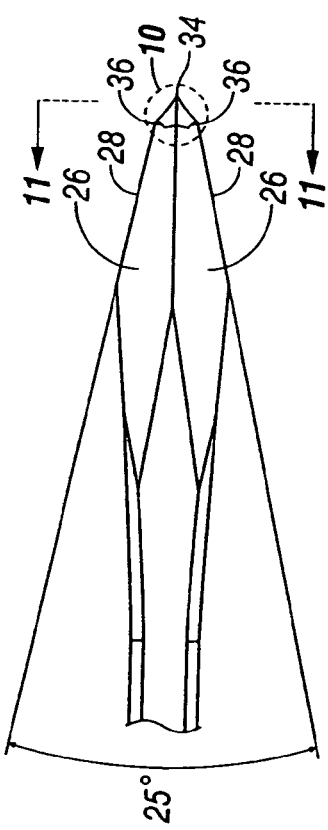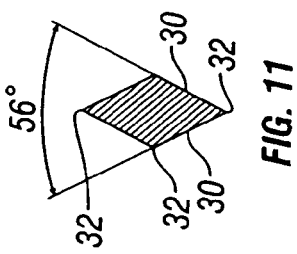

| | | |
|---|---|---|
| Straighten and Cut to Length | /\/ | 100 |
| Coin Point (ceat flash) | /\/ | 110 |
| Form Body (flat press) | /\/ | 120 |
| Form Channel Notch | /\/ | 130 |
| Curve Needle | /\/ | 140 |
| In Process QC | /\/ | 150 |
| Clean Needle | /\/ | 160 |
| Attach to Strip | /\/ | 170 |
| Heat Treat | /\/ | 180 |
| In Process QC | /\/ | 190 |
| Chemical removal of Flash | /\/ | 200 |
| Electro Polish | /\/ | 210 |
| Clean Needle - rinse | /\/ | 220 |
| In Process QC | /\/ | 230 |
| Silicone Coating | /\/ | 240 |
| Remove from Strip | /\/ | 250 |
| Final QA | /\/ | 260 |
| Packaging | /\/ | 270 |
| Overhead | /\/ | 280 |

FIG. 14

SHARPOINT NEEDLE

This application claims the benefit of U.S. Provisional Application No. 60/416,330 filed 4 Oct. 2002.

BACKGROUND

1. Technical Field

The present disclosure relates to a surgical suturing needle for suturing cutaneous and subcutaneous tissue, and in particular, relates to a surgical needle having a multifaceted penetrating needle end characterized by enhanced penetrability and needle hardness.

2. Background of Related Art

Suturing needles for applying sutures, or stitches, by hand in cutaneous and subcutaneous tissue are well known in the art. Typically, the suturing needles are used to close wounds or adjoin adjacent tissue, often at the conclusion of a surgical procedure. Suturing needles are usually made from a cut blank of material such as stainless steel. The cut blank is metal-worked using well known machining techniques to form the suturing needle. The needle generally includes a shaft, a rear end portion with an aperture or channel to secure a suture thread and a needle head at a front end portion for puncturing skin and passing through tissue. The needle head typically incorporates a sharpened needle tip at its distal end and cutting edges. Alternatively, the needle tip may be of a tapered configuration. Straight and curved needles including multiple curved configurations are also known in the art.

An important consideration in the design of surgical suturing needles is needle sharpness. Sharper needles require less force to penetrate tissue and thus cause less tissue trauma. In addition, a sharper needle reduces fatigue on the needle itself, making it less likely to bend or break during suturing. Needle sharpness is typically defined in terms of "penetration force"—the force necessary for a needle to puncture, or penetrate, the tissue. The penetration force is primarily determined by the design and sharpness of the needle point and the cutting edges formed on the needle head. Needle sharpness is also affected by drag force on the needle as it travels through the tissue. The drag force also depends upon the design and sharpness of the needle, and the presence of a lubricating coating.

Another important consideration in needle design and manufacture is to maximize resistance to bending or breakage during use. The strength of a suturing needle is a measure of its ability to resist bending and is determined by such factors as (a) the material of fabrication, (b) the cross-sectional shape of the needle, and (c) the heat treatment applied to the needle during manufacturing. Needle strength should be balanced by needle ductility, which is defined in terms of the ability of the needle to be reshaped after it flexes from its original shape. A surgical needle with good strength characteristics but little or no ductility can be brittle, and may snap and break during use. It is generally known that in working with a metallic material, as the strength of the material increases the ductility will decrease. Therefore, it is desirable to carefully balance the strength and ductility characteristics of a suturing needle.

SUMMARY

Accordingly, the present disclosure is directed to a surgical needle, which includes an elongated needle body defining a longitudinal axis. The elongated needle body includes a main shaft, a needle end adjacent the main shaft, and a needle tip extending from the needle end and having an extreme needle point. The needle end includes a plurality of concave surfaces extending from the needle tip to the main shaft. The needle tip includes a plurality of concave surfaces extending from the needle point to intersect the concave surfaces of the needle end. The concave surfaces of the needle end are obliquely arranged relative to the longitudinal axis at a first angle. The concave surfaces of the needle tip are obliquely arranged relative to the longitudinal axis at a second angle greater than the first angle. The elongated needle body includes cutting edges disposed along lines of intersection of the concave surfaces of the needle end with the concave surfaces of the needle tip.

In a preferred embodiment, the needle end includes four intersecting concave surfaces and defines a generally diamond-shape in cross-section along an axis transverse to the longitudinal axis. The needle end defines a maximum cross-sectional dimension greater than a corresponding maximum cross-sectional dimension of the main shaft. The needle tip may include four intersecting concave surfaces.

The main shaft of the needle end may be curved along the longitudinal axis of the needle body or straight. The main shaft further includes means for attaching a suture.

In another embodiment, a surgical needle includes an elongated needle body defining a longitudinal axis, and having a main shaft, a needle end adjacent the main shaft, and a needle tip contiguously extending from the needle end and having an extreme needle point. The needle end includes at least three non-linear intersecting surfaces extending from the needle tip to the main shaft. The needle tip includes at least three non-linear intersecting surfaces extending from the needle point to the needle end and intersecting the at least three non-linear surfaces of the needle end. The at least three non-linear surfaces of the needle end define cutting edges along lines of intersection of adjacent surfaces thereof. The at least three non-linear surfaces of the needle tip define cutting edges along lines of intersection of adjacent surfaces thereof. The at least three non-linear intersecting surfaces of the needle end and the at least three non-linear intersecting surfaces of the needle tip define cutting edges along lines of intersection thereof.

In a preferred embodiment, the needle end includes four non-linear surfaces and the needle tip includes four non-linear surfaces. The four non-linear surfaces of each of the needle end and the needle tip are generally concave.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 7 is a side plan view of the needle end and the needle tip;

FIG. 8 is an isolated side view adjacent the needle tip;

FIG. 9 is a top plan view of the needle end and the needle tip;

FIG. 10 is an isolated top view adjacent the needle tip;

FIG. 11 is a cross-sectional view taken along the lines 11-111 of FIG. 9;

FIG. 14 is a flow chart depicting the manufacturing process of the surgical needle.

DESCRIPTION OF PREFERRED EMBODIMENTS

Figure 1:
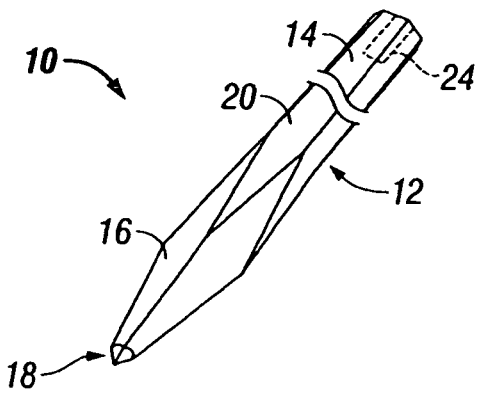
FIG. 1 is a perspective view of the surgical needle in accordance with the principles of the present disclosure.

Preferred embodiment(s) of the surgical needle of the present disclosure will now be described in detail with reference to the drawings wherein like reference numerals identify similar or like elements throughout the several views. As used herein, the term "distal" refers to that portion which is further from the user, while the term "proximal" refers to that portion which is closest to the user.

Figure 2:
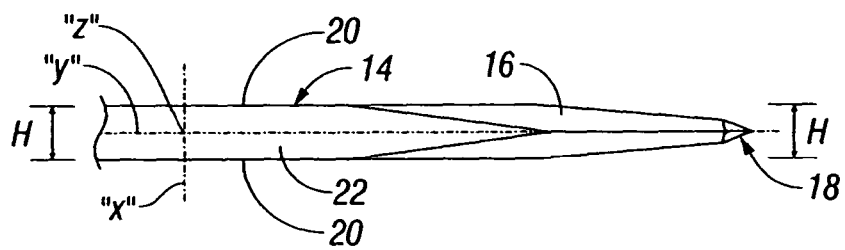
FIG. 2 is a side plan view of the surgical needle of FIG. 1.
Figure 3:
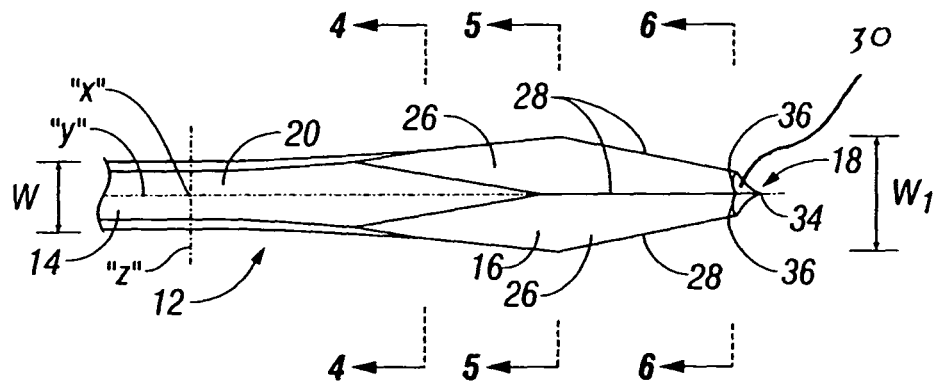
FIG. 3 is an enlarged top plan view illustrating the configuration of the needle end and the needle tip.

Referring now to FIGS. 1-3, the surgical needle of the present disclosure is illustrated. Surgical needle 10 includes elongated needle body 12. Needle body 12 includes main shaft 14, needle end 16 extending from the main shaft 14 and needle tip 18 adjacent the needle end 16. Needle body 12 may be curved along its length through an arc of curvature ranging from about 30° to about 270'. Alternatively, needle body 12 may be straight. Needle body 12 defines longitudinal axis "y" which extends along the length of the needle body 12 and transverse axes "x" and "z". Transverse axes "x" and "z" correspond to the height and width dimensions of needle body 12.

Figure 4:
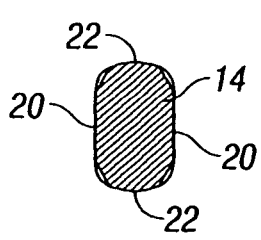
FIG. 4 is a cross-sectional view of the needle end of the surgical needle taken along the lines 4-4 of FIG. 3.

With reference to FIGS. 2-4, in conjunction with FIG. 1, main shaft 14 of needle body 12 is four sided consisting of opposed planar surfaces 20 interconnected by arcuate side surfaces 22. Main shaft 14 defines a height "H" (corresponding to an x-dimension) (FIG. 2) and a width "W" (corresponding to a z-dimension) (FIG. 3). The preferred height to width ratio H/W ranges from about 0.50-1.00, preferably about 0.75. This pronounced ratio greatly increases the strength of the needle. The cross-section of main shaft 14 facilitates handling by the surgeon and manipulation with a needle holder, e.g., needle forceps. Main shaft 14 may also be square in cross-section or circular.

Main shaft 14 includes means for attaching a suture to needle 10. The preferred means includes an enclosed channel 24 (FIG. 1) dimensioned for reception of a suture end of a suture. A blind hole maybe used alternatively for suture reception. Channel 24 or hole may be closed about the suture end through conventional swaging or crimping processes to secure the suture to elongated needle body 12. The dimensioning of channel 24 or hole of main shaft 14 may be selected to provide for permanent (non-detachable) or detachable securement of the suture to needle body 12. The type of securement effectuated is also dependent upon the swaging force employed during the attachment process. It is further envisioned that main shaft 14 may be provided with a U-shaped channel. Alternatively, adhesive suture attachment methodologies are also envisioned.

Figure 5:
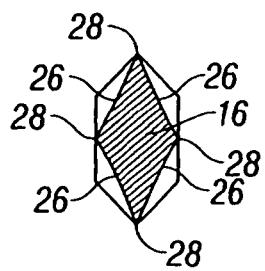
FIG. 5 is a cross-sectional view of the needle end taken along the lines 5-5 of FIG. 3.
Figure 6:
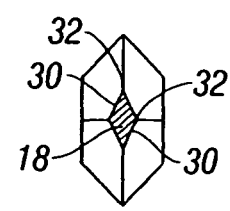
FIG. 6 is a cross-sectional view of the needle tip taken along the lines 6-6 of FIG. 3.

Referring now to FIGS. 2, 3, and 5, needle end 16 will be discussed in detail. Needle end 16 includes an enlarged needle head which is advantageously dimensioned to reduce the penetration force required to penetrate tissue while optimizing needle strength. Specifically, needle end 16 includes a plurality of concave surfaces 26 obliquely and symmetrically arranged relative to the longitudinal axis "y" contiguously extending and outwardly tapering from needle tip 18 to main shaft 14. In embodiments where the needle body is curved, the concave surfaces on the needle end remain in symmetrical alignment with the longitudinal axis. Preferably four concave surfaces 26 are provided to provide a general diamond shape cross-section as depicted in FIG. 5. Adjacent concave surfaces 26 define cutting edges 28 along their lines of intersection. The maximum cross-sectional dimension of needle end 16 is along its approximate mid-section (along lines 5-5 of FIG. 3) and defines a width "W1" greater than a corresponding maximum width "W" of main shaft 14. A preferred ratio of "W1"/W ranges from about 1.5-2.00, preferably about 1.75.

Referring now to FIGS. 2, 3, and 6-11, needle tip 18 will be discussed. Needle tip 18 includes a plurality (preferably four) of concave surfaces 30 arranged at an oblique angle relative to the axis "y" of the needle, remaining in symmetrical alignment with the longitudinal axis, and intersecting to define a general diamond shape in cross-section best depicted in FIG. 11. Adjacent concave surfaces 30 define cutting edges 32 along their lines of intersection. Preferably, concave surfaces 30 taper outwardly relative to the axis "y" at an angle which is greater than the angle of taper of concave surfaces 26 of needle end 16. Concave surfaces 30 of needle tip 18 extend from extreme needle point 34 to concave surfaces 26 of needle end 16 to provide four additional cutting edges 36 at the respective lines of intersection.

As appreciated, by virtue of the configuration of needle end 16 and needle tip 18 at least 12 cutting edges for penetrating tissue are provided, i.e., four cutting edges 30 within needle tip 18, four cutting edges 28 within needle end 16 and four cutting edges 36 at the intersection of the needle tip 18 and the needle end 16. This multiple cutting edge arrangement in combination with the "hollow ground" or concave geometry of surfaces 26, 30 greatly enhances passage of the needle through tissue.

Figure 12:
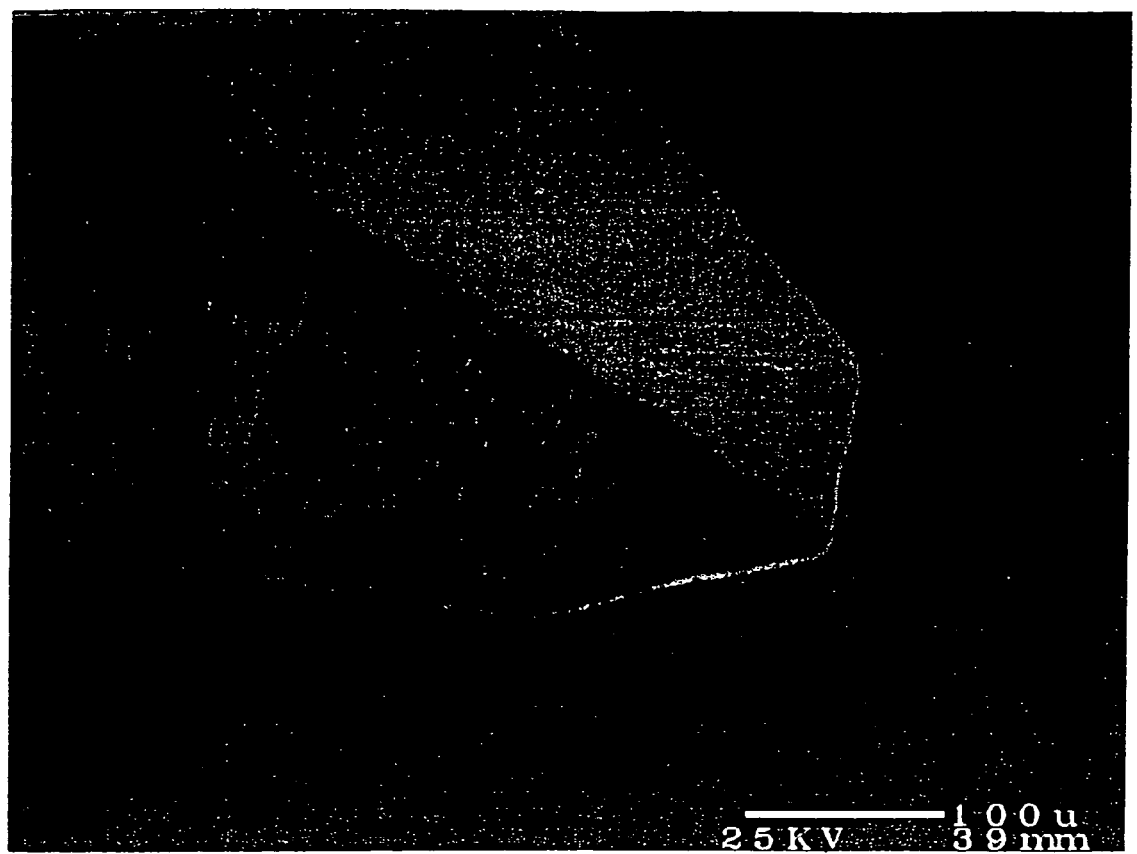
FIGS. 12-13 are photomicrographs of the needle end and the needle tip.
Figure 13:
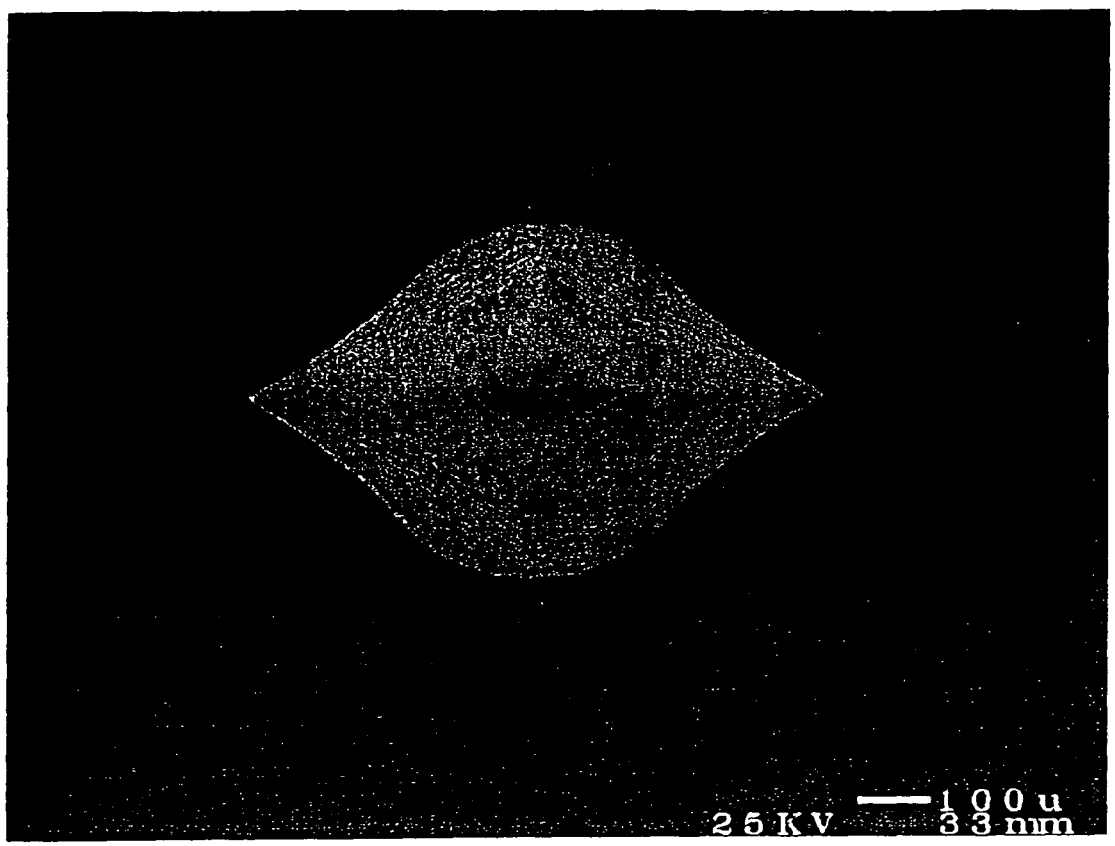

Further details of the surgical needle 10 may be appreciated by reference to the photomicrographs of FIGS. 12-13.

The surgical suturing needle of the present disclosure possesses attributes of primary significance in suturing needles. Specifically, by virtue of the multiple cutting edges, the needle possesses superior needle sharpness and also demonstrates superior strength. Moreover, the cutting edges 28 extend to the widest part of needle end 16 thereby slicing, in conjunction with the remaining edges 32, 36, the tissue as it passes through and providing an opening which is slightly larger than the cross-section of main shaft 14, consequently, significantly reducing the drag force and permitting the shaft 14 to easily pass through the tissue. The flattened cross-section of the main shaft 14 also produces a profile conducive to continued passage of the needle through the tissue.

The choice of materials of surgical needle 10 is made to optimize strength, ductility and resistance to bending or breaking of the needle. However, as noted, the cross-sectional shape and dimensions of the needle contributes significantly to the physical characteristics of the needle. Preferred materials include stainless steel such as series "300" stainless steels, which typically have tensile strengths of between 325,000-350,000 lbs/in.sup.2, attain their high strength from undergoing cold working as the material is converted from an ingot to wire of the desired diameter.

Surgical needle 10 is manufactured through conventional cutting, coining, grinding and/or swaging processes, and may be heat treated to further enhance its strength and resistance to bending.

Needle 10 is manufactured in accordance with the needle process flow described in the flow chart of FIG. 14. Specifically, the steps of manufacture are performed in the sequence of operations inclusive of operation numbers 100-280 described in the needle process flow. These operations include, inter-alia, coining the needle point, flat pressing the needle body, curving the needle, removing excess flash material, electropolishing and coating.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical needle, which comprises:
an elongated needle body defining a longitudinal axis and proximal and distal ends, the elongated needle body including a main shaft adjacent the proximal end and a needle end adjacent the main shaft, the needle end comprising a first distinct set of at least three non-linear intersecting surfaces distally extending from the main shaft and a second distinct set of at least three non-linear intersecting surfaces contiguous with the first set of at least three non-linear intersecting surfaces and extending distally therefrom to an extreme distal needle point, the at least three non-linear intersecting surfaces of the first set and the at least three non-linear intersecting surfaces of the second set defining respective cutting edges along each line of intersection of the first distinct set of at least three non-linear intersection surfaces with the second distinct set of at least three non-linear intersecting surfaces and the needle end defining a maximum cross-sectional dimension greater than a corresponding maximum cross-sectional dimension of the main shaft.

2. The surgical needle according to claim 1 wherein the at least three non-linear surfaces of the first set define cutting edges along lines of intersection of adjacent surfaces thereof.

3. The surgical needle according to claim 2 wherein the at least three non-linear surfaces of the second set define cutting edges along lines of intersection of adjacent surfaces thereof.

4. The surgical needle according to claim 3 wherein the first set includes four non-linear surfaces.

5. The surgical needle according to claim 4 wherein the second set includes four non-linear surfaces.

6. The surgical needle according to claim 5 wherein the four non-linear surfaces of each of the first set and the second set are generally concave.

7. The surgical needle of claim 6 wherein the four non-linear surfaces of the first set are symmetrically arranged about the longitudinal axis and wherein the four non-linear surfaces of the second set are symmetrically arranged about the longitudinal axis.

8. The surgical needle according to claim 1 wherein the at least three non-linear surfaces of each of the first set and the second set are generally concave.

9. The surgical needle of claim 1 wherein the at least three non-linear intersecting surfaces of the first set are symmetrically arranged about the longitudinal axis and wherein the at least three non-linear intersecting surfaces of the second set are symmetrically arranged about the longitudinal axis.

10. A surgical needle, which comprises:
an elongated needle body defining a longitudinal axis and proximal and distal ends, the elongated needle body including a main shaft adjacent the proximal end, a needle end adjacent the main shaft defining a generally diamond-shape in cross-section along an axis transverse to the longitudinal axis and a maximum cross-sectional dimension greater than a corresponding maximum cross-sectional dimension of the main shaft, and a needle tip extending distally from the needle end defining a generally diamond-shape in cross-section along an axis transverse to the longitudinal axis and having an extreme needle point, the needle end including a first distinct set of four generally concave intersecting surfaces extending between the needle tip and the main shaft, the needle tip including a second distinct set of four generally concave intersecting surfaces extending between the needle point and the needle end to intersect the first set of concave surfaces of the needle end, and cutting edges disposed along each respective line of intersection of the first set of four surfaces of the needle end with the second set of four surfaces of the needle tip.

11. The surgical needle according to claim 10 wherein the first set of the four concave surfaces of the needle end are obliquely arranged relative to the longitudinal axis at a first angle.

12. The surgical needle according to claim 11 wherein the second set of the four concave surfaces of the needle tip are obliquely arranged relative to the longitudinal axis at a second angle greater than the first angle.

13. The surgical needle according to claim 10 wherein the main shaft is curved along the longitudinal axis of the needle body.

14. The surgical needle according to claim 10 wherein the main shaft includes means for attaching a suture.

15. The surgical needle of claim 10 wherein the concave surfaces of the first set are symmetrically arranged about the longitudinal axis and wherein the concave surfaces of the second set are symmetrically arranged about the longitudinal axis.

* * * * *